United States Patent [19]
Burgess, Jr.

[11] Patent Number: 5,434,084
[45] Date of Patent: Jul. 18, 1995

[54] FLOW OPTRODE HAVING SEPARATE REACTION AND DETECTION CHAMBERS

[75] Inventor: Lloyd W. Burgess, Jr., Seattle, Wash.

[73] Assignees: The Washington Research Foundation; The Board of Regents of the University of Washington, both of Seattle, Wash.

[21] Appl. No.: 404,285

[22] Filed: Sep. 6, 1989

[51] Int. Cl.⁶ ............... G01N 35/08; G01N 21/01
[52] U.S. Cl. ...................... 436/52; 128/634; 356/41; 422/68.1; 422/52; 422/82.05; 422/82.06; 422/82.07; 422/82.08; 436/172; 436/177; 436/178
[58] Field of Search ............ 422/68.1, 82.05, 82.06, 422/82.07, 82.08, 52; 436/172, 52, 177, 178; 128/633, 634, 635, 636, 673; 356/39, 40, 41

[56] References Cited

U.S. PATENT DOCUMENTS

| | | | |
|---|---|---|---|
| 3,679,312 | 7/1972 | Mansberg | 422/52 X |
| 4,200,110 | 4/1980 | Peterson et al. | 128/634 |
| 4,265,249 | 5/1981 | Schindler et al. | 128/635 |
| 4,344,438 | 8/1982 | Schultz | 128/634 |
| 4,476,870 | 10/1984 | Peterson et al. | 128/634 |
| 4,509,370 | 4/1985 | Hirschfeld | 73/705 |
| 4,577,109 | 3/1986 | Hirschfeld | 422/82.07 X |
| 4,594,504 | 6/1986 | Coursolle et al. | 250/227 |
| 4,771,006 | 9/1988 | Miller et al. | 436/126 |
| 4,803,992 | 2/1989 | Lemelson | 128/634 |
| 4,844,887 | 7/1989 | Galle et al. | 422/65 |
| 4,929,561 | 5/1990 | Hirschfeld | 422/82.06 |
| 4,954,318 | 9/1990 | Yafuso et al. | 422/82.08 |
| 4,960,711 | 10/1990 | Aoki et al. | 436/172 X |
| 5,176,881 | 1/1993 | Sepaniak et al. | 422/82.06 X |

FOREIGN PATENT DOCUMENTS

| | | |
|---|---|---|
| 190111 | 8/1986 | European Pat. Off. . |
| 242279 | 1/1987 | Germany . |
| 972397 | 11/1982 | U.S.S.R. ............... 422/52 |

OTHER PUBLICATIONS

S. G. Schulman, "Molecular Luminescense Spectroscopy", *Chemical Analysis*, 77(2):151-155 (1985).
S. Luo and D. R. Walt, "Fiber-Optic Sensors Based on Reagent Delivery with Controlled-Release Polymer", *Anal. Chem*, 61:174-177 (1989).
S. H. Lieberman et al., "Fiber Optic-Fluorescence Sensors for Remote Detection of Chemical Species in Seawater", *Proceedings of the Symposium on Chemical Sensors*, 87-9:464-475 (1987).
S. M. Inman et al., "Pressurized Membrane Indicator System for Fluorogenic-Based Fiber-Optic Chemical Sensors", *Analytica Chimica Acta*, 217:249-262 (1989).
W. R. Seitz, "Chemical Sensors Based on Immobilized Indicators and Fiber Optics", *CRC Critical Reviews in Analytical Chemistry*, 19(2):135-173 (1988).
W. R. Seitz, "Chemical Sensors Based on Fiber Optics", *Analytical Chemistry*, 56(1): 16A-34A (1984).
S. M. Angel, "Optrodes: Chemically Selective Fiber-Optic Sensors", *Spectroscopy*, 2(4):38-49 (1987).
E. Labeyrie et al., "Photoelectrode with a Very Short Time-Constant for Recording intracerebrally Ca²⁺ Transients at a Cellular Level", *Journal of Neuroscience Methods*, 1:35-39 (1979).
J. Sepaniak et al, "Design Considerations for Antibody-Based Fiber Optic Chemical Sensors", ANYL abstract 1989.

*Primary Examiner*—James C. Housel
*Assistant Examiner*—Arlen Soderquist
*Attorney, Agent, or Firm*—Seed and Berry

[57] ABSTRACT

There is disclosed a device capable of continuously measuring the presence and concentration of an analyte or analytes and a method for using said device in a liquid and/or a gas phase reaction volume. The inventive device comprises a sensor probe, a reservoir, and a detector. The inventive device delivers reagent to the sensor probe in a flow method to directly and continuously renew reagent, thereby allowing the continuous measurement of the presence and the concentration of an analyte or analytes.

23 Claims, 6 Drawing Sheets

FLOW OPTRODE HAVING SEPARATE REACTION AND DETECTION CHAMBERS

STATEMENT OF GOVERNMENT INTEREST

This invention was made with government support under Grant No. EEC84-15075 awarded by the National Science Foundation. The government has certain rights in the invention.

TECHNICAL FIELD OF THE INVENTION

The present invention relates to a device and a method to continuously measure the presence and concentration of an analyte or analytes in a liquid and/or a gas phase. The invention utilizes a flowing reagent that reacts with the analyte or analytes and the reaction product is detected in an optical sensor device. The reagent can use irreversible chemistry and reagent renewal is under direct and continuous control.

BACKGROUND OF THE INVENTION

Fiberoptic-based chemical sensor devices are becoming established analytical tools for remote and in situ chemical sensing. The ideal optical sensor device must have the ability to measure the concentration of an analyte continuously through changes in the optical properties of the sensing reagent. For example, for oceanographic and environmental sampling, conventional methods for measuring nutrient distributions, species of geochemical interest, and toxic chemicals usually require cumbersome discrete sampling techniques. The required sample handling and processing techniques are often time-consuming and labor-intensive and are subject to contamination and storage problems. Because samples are often processed days or weeks after collection, these techniques are not well-suited for mapping distributions of chemical constituents in dynamic aquatic environments. Sensors are needed that can be deployed in situ for the rapid, remote measurement of chemical species in aquatic samples.

Many colorimetric or fluorometric techniques are irreversible because they form a tight binding complex or utilize reagents that generate an irreversibly colored adduct. Irreversible sensors can be used if they operate in an integrating mode; however, they must be replenished frequently with fresh sensing reagent. Accordingly, it is often difficult to reuse the same sensor probe for a large number of measurements or for the continuous measurement of an analyte.

Many fiberoptic-based chemical sensors have been developed to attempt to continuously measure the presence and concentration of an analyte or analytes in a moving process stream. Many devices use an immobilized reagent to render them specific for an otherwise optically undetectable analyte of interest. These devices are often called "optrodes." Most optrodes have been limited to reversible reagent chemistries, because irreversible reagent reactions will severely limit the lifetime of the optrode probe and cause calibration problems. Moreover, the optrodes cannot use the vast number of irreversible reagent chemistries that form complex formations and colored products upon reaction with an analyte. Moreover, the optrodes with reversible reagent chemistries have had difficulties regarding probe-to-probe reproducibility, limited dynamic ranges, reagent photolability and leaching, and slow response times.

One approach to this problem was developed by Luo et al., "Fiber-Optic Sensors Based On Reagent Delivery with Controlled-Release Polymers," *Anal. Chem.* 61:174–77 (1989). Luo et al. describe a polymeric delivery system that attempts to deliver fresh sensing reagents for extended periods using a reversible sensing reagent. The Luo et al. probe releases the reversible reagent, entrapped in an ethylene-vinyl acetate polymer matrix, to the probe tip upon contact with an aqeuous solution. Several problems noted by Luo et al. included the observation that when the polymer was below the fiber tip, the emerging light from the fiber was reflected by the polymer surface and part of this reflected light reentered the fiber, resulting in a systematic error in the signal. Further, the Luo et al. design resulted in the buildup of a large concentration gradient of dyes around the polymer.

Another attempt by Inman et al., "Pressurized Membrane Indicator System for Fluorogenic-Based Fiber-Optic Chemical Sensors," *Analytica Chimica Acta*, 217:249–62 (1989), describes a fluorogenic indicator that is forced through an ultrafiltration membrane into the analyte solution. The reaction product between the reagent and the analyte (in this case an indicator molecule and a target ion, respectively) occurs at the membrane/solution interface. Light from a bifurcated fiber-optic cable stimulates fluorescence and fluorescence emission from the membrane/solution interface is transmitted back up the cable to a photodiode detector. The Inman et al. sensor has an element of renewability by continually renewing the indicator (reagent) at the end of the fiberoptic probe. However, the buildup of the reaction product on the membrane/solution interface again limits the usefulness of this sensor probe.

Accordingly, there is a need in the art to develop a completely renewable reagent sensor probe that can utilize the full spectrum of irreversible reagent chemistries as well as reversible reagent chemistries.

SUMMARY OF THE INVENTION

The present invention is directed to a device capable of continuously measuring the presence and concentration of an analyte or analytes in a liquid or gas phase, such as in a process stream, comprising a sensor probe, a reservoir, and a detection means. The sensor probe comprises a reaction chamber defined by a permeable membrane. The sensor probe has an inflow opening, an outflow opening, a primary electromagnetic radiation source directed within the sensor probe, and a detection fiber. The primary electromagnetic radiation source directs electromagnetic radiation across a defined path within the reaction chamber toward the detection fiber. A reagent flows into the reaction chamber from the inflow opening, across the defined path, and out the outflow opening. Analyte or analytes diffuse across the permeable membrane into the reaction chamber, react with the reagent flowing within the reaction chamber of the sensor probe, and modulate electromagnetic radiation across the defined path. The reservoir communicates with the inflow opening of the sensor probe and contains the reagent in a liquid or gaseous state of matter. The reservoir feeds the inflow opening by a pumping means, or by gravity flow with a valve means to control flow rate. The reagent will chemically react with the analyte or analytes within the reaction chamber of the sensor probe to create a reaction product that modulates electromagnetic radiation differently from the unreacted reagent. The detection means communicates with the detection fiber in the sensor probe and measures the intensity of electromagnetic radiation that is directed across the defined path within the sensor probe, or that is generated by the reaction product, such as with chemiluminescence. Preferably, the electromagnetic radiation signal is modulated and the detection means demodulates the signal.

In another embodiment, the reaction chamber is divided into two chambers. The first chamber is a reaction chamber defined by the permeable membrane and containing the inflow opening communicating with the reservoir. The second chamber, or detection chamber, is downstream from the first chamber and communicating with the first chamber. The second chamber comprises the electromagnetic radiation source, the detection fiber, and the outflow opening. The second chamber can be defined by any enclosed space communicating with the first chamber and a waste reservoir or waste for the ultimate destination of the reagent through the outflow opening.

The permeable membrane can be either a semipermeable membrane or an ion exchange membrane. The semipermeable membrane allows the analyte or analytes to diffuse across the membrane by passive diffusion based upon molecular size and the ion exchange membrane transports the analyte or analytes by an ion exchange diffusion based upon charge and possibly size.

Preferably, the device further comprises a secondary source of electromagnetic radiation within the sensor probe. The secondary source is a means for scattering and/or reflecting electromagnetic radiation from the primary electromagnetic radiation source. When a secondary source of electromagnetic radiation is present within the sensor probe, the defined path becomes the distance from the secondary source to the detection fiber. Light or electromagnetic radiation from the primary source is carried, via optical fiber, to the secondary source. The secondary source acts to redirect the electromagnetic radiation from the primary source so that it can be collected by the detection fiber after traversing the defined path.

The reagent can use irreversible chemistry or reversible chemistry when binding to or reacting with the analyte. The reagent modulates or emits electromagnetic radiation upon reaction with or binding to the analyte. The electromagnetic radiation is preferably selected from the group consisting of UV light, visible light, or IR light. Examples of reagents utilizing irreversible chemistry are known to those of ordinary skill in the art and are described in, for example, J. Ruzicka and E. Hansen, "Flow Injection Analysis," Vol. 62 in *Chemical Analysis*, 2nd ed , J. Wiley and Sons, NY, N.Y. (1988) and E. Jungreis, "Spot Test Analysys: Clinical, Environmental, Forensic and Geochemical Applications," Vol. 75 in *Chemical Analysis*. Further, the reaction product of the reagent and the analyte can create a fluorescent reaction product that absorbs light of one wavelength and emits light of a different wavelength.

In another embodiment, the inventive device is capable of continuously measuring the presence and concentration of an analyte or analytes in a liquid or gas phase by chemiluminescence. The device does not contain a primary or secondary source of electromagnetic radiation because the chemiluminescent reaction product emits photons. The photons are detected by the detection fiber. The detection fiber communicates with a detection means that can quantitate the concentration of analyte or analytes according to the intensity of the light emission or the wavelength of the photons emitted.

In yet another embodiment of the present invention is a device capable of continuously measuring the presence and concentration of an analyte or analytes in a reaction volume, such as a process stream. This embodiment is used when the analyte or analytes or reaction volume can or tend to foul the permeable membrane, thus preventing continued diffusion of the analyte or analytes across the permeable membrane. The device that measures the analyte or analytes in a reaction volume comprises a sensor probe, a reservoir, and a detection means. The sensor probe comprises a reactant inflow tube, a primary electromagnetic radiation source and a detection fiber. Therefore, the sensor probe does not contain a reaction chamber defined by a permeable membrane, because the reactant flows directly into the reaction volume or process stream containing the analyte or analytes to be detected, and the reaction product diffuses or is swept away by the process stream. Alternatively, the reaction chamber is defined by impermeable walls with an open end communicating with the analyte containing liquid or gas. The probe contains an outflow opening at a lower pressure than the inflow opening so as to be able to remove the reaction product and unreacted reagent from the reaction chamber.

The primary electromagnetic radiation source is directed in a defined path within the reaction volume to the detection fiber. The inflow tube directs a flow of a reactant into the reaction volume, across the defined path and out the outflow tube. It is not necessary that all or even substantially all of the reactant (either unreacted or reacted with the analyte or analytes) gets removed by the outflow tube. Preferably, the outflow tube has a larger cross-sectional area than the inflow tube.

The reservoir communicates with the inflow tube and contains the reagent in a liquid or a gaseous state of matter. The reagent chemically reacts with the analyte or analytes in the reaction volume or process stream. The flow of reagent and/or analyte or analytes in the process stream is directed across the defined path. Chemically reacted reagent can modulate electromagnetic radiation differently than unreacted reagent. This is detected by changes in the wavelength and/or intensity of the electromagnetic radiation in the detection fiber.

The detection fiber communicates with a detection means that can quantitatively and qualitatively measure the intensity and/or wavelength of electromagnetic radiation reaching the detection fiber. This embodiment, without a permeable membrane, can further comprise a secondary source of electromagnetic radiation. The secondary source of electromagnetic radiation is a means for scattering and/or reflecting electromagnetic radiation from the primary electromagnetic radiation source. When a secondary electromagnetic radiation source is present, the defined path becomes the distance from the secondary source to the detection fiber. Preferably, the defined path is located across the process stream or across the flow path of reagent from the inflow tube to the outflow tube and within the reaction chamber.

The present invention is further directed to a method for continuously measuring the presence and concentration of an analyte or analytes in a liquid or gas. Preferably, the method involves measuring the presence and concentration of an analyte or analytes in a liquid or gas process stream. The method comprises contacting the sensor probe with a liquid or gas, adjusting the flow rate of the reagent into the sensor probe which adjusts the sensitivity and useable measurement range of the sensor probe, and detecting the presence and concentration of the analyte or analytes by measuring the reaction product of the reagent and the analyte or analytes according to a modulation of electromagnetic radiation or by chemiluminescence.

The utility of the present invention allows for the use of irreversible reagent chemistries which have been developed to a greater extent than the reversible reagent chemistries. Further, the sensor probe can be used continuously because the reagent is continuously renewed by flowing through the sensor probe. The device is compatible with numerous spectroscopic techniques including, but not limited to, absorbance, luminescence, chemiluminescence, fluorescence and light scattering for the analyte modulation of the optical signal. The control of the composition of delivered reagent and reagent flow rate allows for continuous adjustment of the dynamic sensitivity range of the probe for a given analyte while the probe is located in situ. Further, the probe has multiple analyte capability because the same probe can be used for a variety of different analytes simply by changing the nature and/or concentration of the reagent in the reservoir. Moreover, a small physical volume of the reaction chamber in the sensor probe (e.g., less than 5 $\mu$l) provides for a short diffusion path of the analyte across the permeable membrane and a rapid response time due to the rapid mixing of the analyte and reagent flowing out of the inflow opening. Further, when a reference fiber is employed in the probe, the dual beam geometry helps to correct nonanalyte-related modulation of the optical signal at a given wavelength of electromagnetic radiation.

Preferably, the device modulates the electromagnetic radiation signal into probe and demodulates the signal at the detection means. Nonanalyte-related modulation of the signal may be caused by changes in the intensity of radiation emanating from the primary source, or losses, induced by bending or other means, by the optical fiber which transmits the primary source radiation to the probe head. The reference fiber allows correction for this modulation so that it is not falsely interpreted as a change in analyte concentration.

BRIEF DESCRIPTION OF THE DRAWINGS

FIG. 2 is a schematic of the sensor probe of FIG. 1 communicating with a series of other elements. The inflow tube (6) communicates with a pump and/or a reservoir that contains the reagent in a liquid or gaseous state of matter. The outflow tube (7) communicates with waste. The primary source of electromagnetic radiation (1) is a fiberoptic cable that communicates with a source of electromagnetic radiation and a modulator. The detection fiber (5) and the reference (2) communicate with a signal detector and a reference detector, respectively. Both the signal detector and the reference detector communicate with a demodulator and the signals are analyzed by computer.

DETAILED DESCRIPTION OF THE INVENTION

The present invention relates to a device and a method for continuously measuring the presence and the concentration of an analyte or analytes in a liquid or gas phase. Preferably, the analyte or analytes are located in a process stream, wherein the inventive device is capable of continuously monitoring the concentration of a critical analyte so as to provide data to monitor the process and adjust various process parameters, as necessary.

The invention is a flow optrode. Optrodes are optical transducers used at the distal end of an optical fiber, which provide for chemical analytical specificity in a remote fiber spectroscopy measurement. Chemical optrodes respond to changes in chemical concentrations of an analyte or analytes. Classic chemical optrodes use entrapped or immobilized reagents at the fiber tip that react with an analyte in such a way that an optical signal is produced, or an existing optical signal is modulated in response to changes in the analyte concentration. The classical optrode usually consists of a reagent indicator with unique absorption or fluorescence properties that change as a function of sample concentration. The optrode is read by sending a probe beam down the optical fiber and monitoring the light that returns back up the fiber or up a separate return fiber. For an absorption optrode, the attenuation of the probe beam is related to the sample concentration, while in a fluorescent optrode, the intensity, frequency, or some other characteristic of the fluorescence emission is used to monitor sample concentration.

Optrode measurements are usually made in either one of two ways, by monitoring attenuation in the probe beam at one or more wavelengths, or by monitoring fluorescence generated by the probe beam. The probe beam comprising a single wavelength or a wavelength region of electromagnetic radiation can be attenuated by a number of different mechanisms, including absorption, scattering, and reflection at the fiber surface. The measurements are made by a detection means. Preferred detection means include, for example, a photomultiplier tube and a solid state photodetector.

The type of fiber used will depend upon the application. Optical fibers should be selected according to usable ranges of wavelengths, inherent fiber fluorescence, length of fiber, and cost. For remote measurements of distances greater than 100 meters, the selection of the fiber is important. Fibers are available that cover most of the spectral region of the electromagnetic radiation spectrum from the ultraviolet (220 nm) to the near-infrared. A typical fiber optic has a diameter of approximately 200 $\mu$m. Fibers ranging from 50 $\mu$m to 500 $\mu$m in diameter are preferred for use with the flow optrode in order to keep the flow optrode probe volume small.

The materials used in optical fibers must be both flexible and transparent. The fiber must have a core that is surrounded by a physically compatible cladding with a lower refractive index. Both glasses and plastics can be used. Low-melting silicate glasses are appropriate for fiber fabrication but are limited to transmission in the visible range of the electromagnetic spectrum. Further, silicate glasses are not suitable for longer range transmission of light. Silicate glasses typically have core diameters of from 100 to 200 $\mu$M. Silica fiber can also be coated with a transparent plastic such as a silicone polymer or FEP Teflon ®. Plastic clad silica, often referred to as PCS, has a higher numerical aperture (NA) and is transparent in the ultraviolet (UV) range. Plastic fibers do not transmit light as efficiently as glass or silica fibers but are inexpensive and can be fabricated with larger core diameters. The transmission characteristics depend upon the particular plastics or glasses used in the fiber.

The problem with the fixed reagent optrodes has been the short life span of the usefulness of the sensor probe when irreversible reagent chemistries are used. The first attempt to solve this problem was to develop reversible reagent chemistries. However, reversible reagent chemistries limit the number of analytes that can be determined and the chemical specificity of the probe. The present invention solves this problem by directly controlling the renewal of the reagent in the sensor probe. This is done by flowing reagent in a liquid or a gas medium from a reservoir into the reaction chamber of the sensor probe and out again to a waste collection.

The analyte or analytes from the process stream or sample diffuse across the permeable membrane which defines, in part, the reaction chamber. The permeable membrane can allow diffusion of the analyte or analytes into the reaction chamber by a passive diffusion process with a semipermeable membrane creating some degree of specificity for the analyte or analytes by only allowing molecules of a specific size or chemical type to pass through. Alternatively, the permeable membrane can be an ion exchange barrier that will only allow an analyte or analytes to pass into the reaction chamber based upon their charge and size. Examples of semipermeable membranes for passive diffusion based on size or type include, but are not limited to silicone rubber, porous polypropylene, such as Celgard X-20 or X-10, and porous teflon. Each of the semipermeable membranes have pore sizes that control the movement of molecules based on the size of the molecules. For example, the pore size may range from about 0.05 $\mu$m to about 10 $\mu$m. The permeable membrane may also be an ion exchange membrane to separate analytes by size and charge. More specifically, anion exchange membranes include aminated polystyrene, divinyl benzene, aminated polypropylene, aminated polyethylene, other aminated polymers and other polymers with functional groups, such as trimethyl amine, ethyl dimethyl amine, and dimethyl ethanol amine. Cation exchange membranes include Nafion ®, and sulfonated polystyrene, polyacrylates and polypropylene. The ion exchange membrane can also comprise radiation grafted polymers such as polypropylene, polyethylene, and polystyrene, with various charged functional groups.

The choice of the semipermeable or ion exchange membrane depends upon the molecular size and charge characteristics of the analyte or analytes to be detected. It is within the scope of the present invention to have a hybrid membrane comprising a section of semipermeable membrane and a section of ion exchange membrane such that two or more different analytes may pass into the reaction chamber for detection by one or a plurality of reversible or irreversible reagents.

The sensor probe comprises a reaction chamber defined by the permeable membrane, and inflow opening, an outflow opening, a primary electromagnetic radiation source and a detection fiber. The primary electromagnetic radiation source directs electromagnetic radiation across a defined path within the reaction chamber toward the detection fiber. For example, the primary electromagnetic radiation source can be ultraviolet, visible, or infrared light. Alternatively, the electromagnetic radiation can be an excitation wavelength of light that will allow a fluorescent molecule to emit light at a different wavelength.

The inflow opening communicates with a reservoir containing the reagent in a liquid or a gas state. The reservoir can be located within the sensor probe or external to the sensor probe but communicating with the sensor probe by the inflow opening. The outflow opening communicates with waste or an outflow reservoir that then stores the used reagent for disposal.

The greater the path length, the greater the sensitivity of the sensor probe. Therefore, for measuring low concentrations of analytes, it may be desirable to increase the path length for electromagnetic radiation in the sensor probe and reaction or detection chambers to create a longer defined path length.

Figure 6:
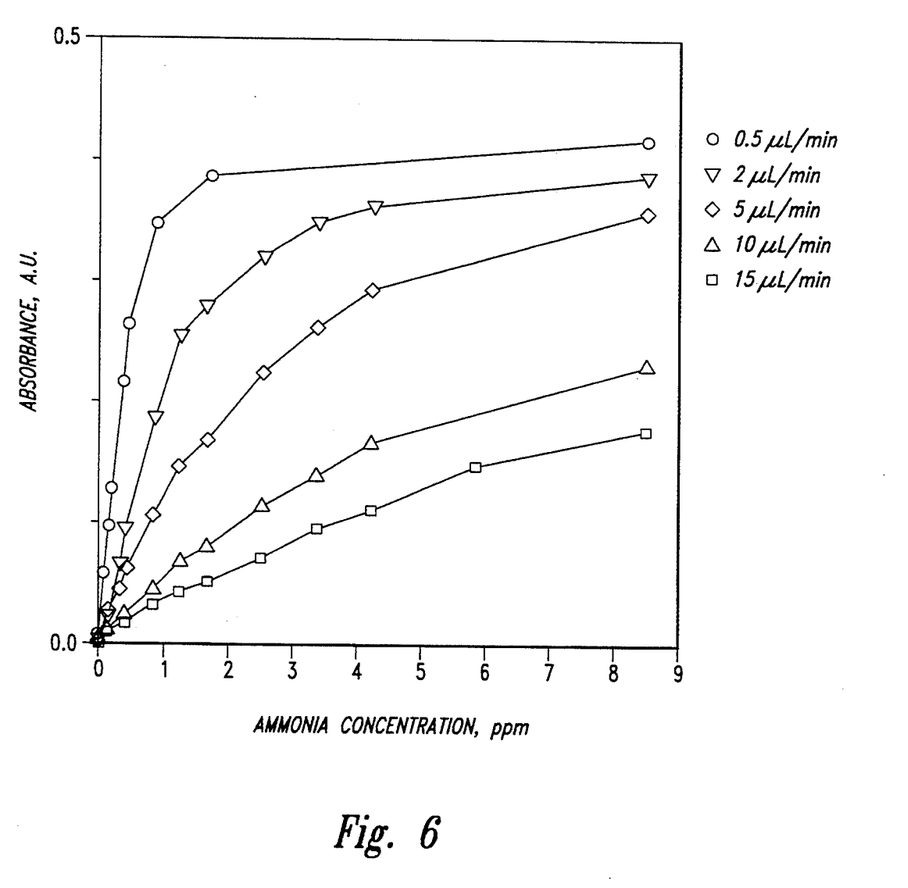
FIG. 6 shows a plot of the response of the probe constructed in Example 1 to varying concentrations of ammonia in aqueous solution. The response is shown at several reagent flow rates showing differential sensitivity and dynamic range as a function of reagent delivery rate.

The reagent delivery flow rate has an effect upon the sensitivity of the sensor probe and the dynamic range of analyte concentration under which the probe operates. For a given external concentration of an analyte, such as ammonia, the amount of time that the analyte has to diffuse across the permeable membrane and interact with the internal reagent solution is important. The interaction time is a function of the volumetric flow rate of the reagent solution through the reaction volume. A slower flow rate will result in a larger absorbance signal than a faster flow rate. This is illustrated in FIG. 6, which shows the probe of Example 1 response to various ammonia concentrations at five different reagent delivery flow rates (0.5, 2, 5, 10, and 15 $\mu$L/min.). The slower flow rates offer the advantage of increased sensitivity, while at faster flow rates the probe is useful over a larger dynamic range.

By continuously renewing the reagent in the probe, the response and recovery times are improved over static reagent sensors. The reagent flow in mixing within the probe, creates a steep gradient in the chemical potential of the analyte across the permeable membrane interface, which results in a rapid steady state concentration. Using an ammonia probe, such as the one described in Example 1, and the reagent bromothymol blue (BTB), response times (to 95% of the steady state signal) ranged from 15 to 40 seconds. The longest response times were observed at lower analyte concentrations and slower flow rates. As the flow rate increased, the response time decreased. Recovery time was also reduced. There was no need to wait for the analyte to diffuse out of the membrane, since the products of the interaction were simply washed out of the sensing volume with fresh reagents.

Using the ammonia sensor of Example 1 with BTB as the reagent, recovery times to base line ranged from 10 to 140 seconds, with the slowest recovery observed at the lower flow rates and at higher concentrations of ammonia. As the flow rate increased, a point was reached where the reagent within the probe, was replaced so rapidly that the analyte concentration made little difference in the rate of recovery.

It is also possible to configure the flow optrode to have a stop flow mode for the flow rate of the reagent. The stop flow mode will attain maximum sensitivity. If the flow rate is sufficiently fast, there will be no response to external analyte concentrations. When the flow is stopped, the analyte diffuses through the permeable membrane at a rate determined by the external analyte concentration. The slope of the increase in absorbance is a function of the external analyte concentration. Alternatively, the reagent pump can be stopped for a specified period of time, and the signal level at that time is related to analyte concentration. Once a slope or a point has been determined, the reagent pump can be turned on again and the signal will return to base line. In this mode, the flow optrode is self-referencing. Using a pH of 5.3, and a reagent concentration of 50 $\mu$M BTB, ammonia as the analyte, and a renewal rate of 15 $\mu$L/min., several aqueous ammonia (analyte) samples were determined with this method. For each determination, the pump was stopped for exactly three minutes, a value taken, and the pump restarted to return the signal to the base line.

The concentration of reagent also affects the sensitivity of the flow optrode. When using BTB as a reagent and ammonia as the analyte and a flow rate of 5 $\mu$L/min. in the flow optrode described in Example 1, the sensitivity of the probe increased as the BTB reagent concentration decreased. One explanation why the sensitivity decreased as the reagent concentration increased is that the reagent also acted as a buffer. Therefore, as the concentration of the reagent increased, so did buffer capacity. As a result, the flow optrode became less sensitive to small changes in analyte concentrations. This effect should only hold when the reagent also acts as a buffer.

The flow rate is adjusted by a valve or by the pump speed within the fluids system of the sensor probe. The fluidics system comprises the reservoir, the communication means with the inflow opening of the sensor probe, the outflow opening of the sensor probe, and a waste reservoir communicating with the outflow opening.

The pump and/or valve system that controls the flow rate and the ability to stop the flow can be located between the reagent reservoir and the inflow opening or between the outflow opening and the waste reservoir. For example, it is possible to deliver reagent in a liquid state with a high precision microinjection pump such as the model CMA/100 from Carnegie-Medicin (Solna, Sweden) when the reagent flow rate is relatively low (e.g., from about 0.1 $\mu$l/min. to about 20 $\mu$l/min.). The reagent reservoir can communicate with the inflow opening with tubing such as Teflon ® tubing or a fused silica capillary (e.g., Model TSP100/170, Polymicro Technologies). The fused silica capillary can have dimensions, for example, of 100 $\mu$m internal diameter and 165 $\mu$m outer diameter. The diameter of the tubing is further used to control the flow rate, with larger innerdiameter tubing being capable of having a faster flow rate.

In summary, the inventive flow optrode can adjust the sensitivity and dynamic range to the concentration of the analyte or changes in concentration of the analyte by varying the flow rate, the reagent composition, or by operating in a stop flow mode. Therefore, the inventive device and the inventive method for using the inventive device offer significant advantages over previously developed optrodes.

For example, reagent photodecomposition and leaching result in limited lifetimes and calibration problems when an immobilized reagent is used within a conventional sensor probe. The inventive device, however, avoids this problem by renewing the reagent within the reaction chamber with fresh reagents as required. While it is possible to adjust the sensitivity and dynamic range of conventional optrodes by varying the reagent composition, a new probe must be constructed in each case. On the other hand, the present inventive flow optrode is able to change reagent reservoirs to change the reagent chemistry without having to construct a new sensor probe.

Response and return times greater than five minutes are common for conventional optrodes. The response and return times can be significantly improved with the flow optrode. Response times are rapid as a result of the steep gradient in analyte concentration created by the reagent flow. Recovery times are relatively fast because the reacted products of reagent and analyte are simply washed out of the reaction chamber with fresh reagents.

Irreproducible construction of conventional optrodes is often the result of physical differences of the substrate on which the reagent is immobilized, and/or different reagent loadings from probe to probe. However, the flow optrode has a standard physical design and can be constructed reproducibly without the variable nature of the reagent loading being a factor. The reagent composition will be reproducible so long as the composition of the reservoir, from which the reagent is pumped, is prepared reproducibly.

Another significant advantage of the flow optrode is its ability to be used with both reversible and irreversible reagent chemistry. In previous optrodes, based upon irreversible reaction, a large reagent reservoir was needed to supply reagent over the desired lifetime of the probe. This has several disadvantages, including a limited lifetime at high analyte concentration. The flow optrode, however, allows an irreversible reagent/analyte reaction to occur and the device can be simply reset with fresh reagent as the reaction products are removed from the reaction chamber through the outflow opening and carried off to waste. The extent of irreversible reagent chemistries is greater than known reversible reagent chemistries. Further, irreversible reagent chemistries exhibit higher binding constants in their detection reactions. Therefore, the proper choice of the permeable membrane for analyte selectivity, the proper choice of the specific reagent chemistry to further analyte selectivity, the proper choice of flow rate or stopped flow mode to further analyte selectivity, and the proper choice of spectral analysis can allow flow optrodes to be prepared for a wide variety of analytes and analyte concentrations.

The reagent is designed to interact with the analyte so as to render it detectable through the detection fiber. The reactant directly or indirectly reacts with the analyte to form an optically detectable product. Alternatively, the reactant can be a catalyst to accelerate the rate at which analyte is converted to an optically detectable product or the reagent can be a substrate for the detection of catalysts. Further, the reagent can be an adsorbent or extractant to preconcentrate an optically detectable analyte within the defined path to modulate the electromagnetic radiation.

Many reagents are indicators that change color upon interacting with the analyte. The measurement is the change in color rather than a change in the intensity of a single color. Thus, the primary source of information is the spectral shift accompanying a reaction between an indicator reagent and an analyte. Examples of indicator type reagent reactions are an acid-base reaction to analyze pH, carbon dioxide, and ammonia.

A complexation type of indicator reaction can be used to measure the concentration of aluminum (III). A ligand exchange can measure the concentration of water vapor and oxygen. Luminescence can measure oxygen as an analyte, and a quenching reaction can measure halide-type analytes. Other reagents include phenol red and the trisodium salt of 8-hydroxy-1,3,6-pyrenetrisulfonic acid (HPTS) as pH indicators. HPTS is a fluorescent reagent. Other pH reagents include 7-hydroxycoumarin-3-carboxylic acid, fluoresceinamine, fluorescein and derivatives.

A carbon dioxide sensor can use both phenol red and HPTS as reagents plus 4-methylumbelliferone. Oxygen sensors are often based on fluorescence quenching with pyrenebutyric acid as the preferred indicator. Glucose may be analyzed by a combination reagent that includes glucose oxidase and a fluorophor sensitive to oxygen quenching. The glucose oxidase-catalyzed oxidation of glucose consumes oxygen to reduce steady-state oxygen concentrations in the reagent phase, which leads to increases in observed fluorescence intensity.

Figure 1:
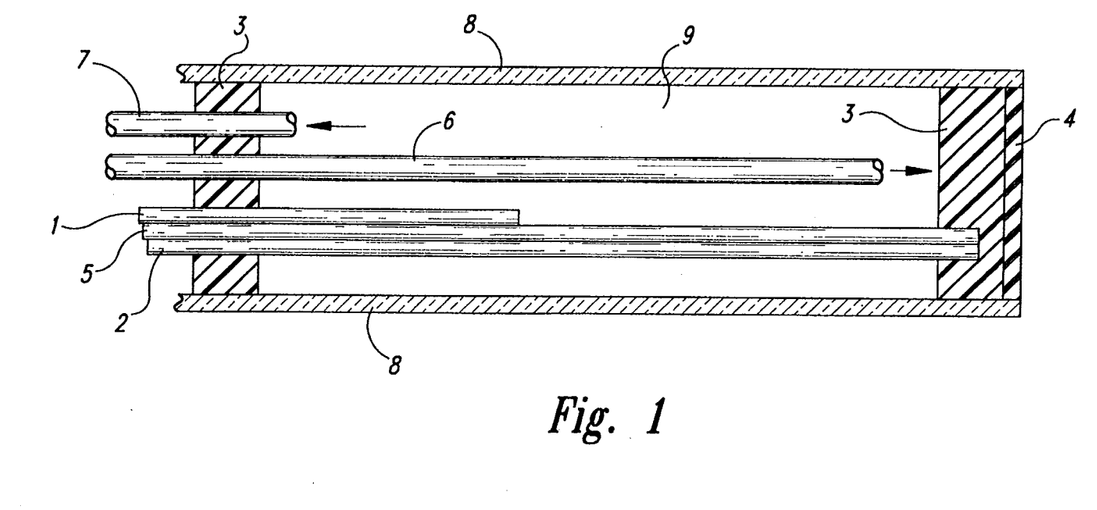
FIG. 1 shows a schematic of one embodiment of a sensor probe showing the reaction chamber (9), inflow tube (6), outflow tube (7), electromagnetic radiation source fiber (1), detection fiber (5), reference fiber (2), an end cap which acts as a secondary source of electromagnetic radiation (4) and consists of a translucent material (3) and may further contain a reflecting overlayer, and permeable membrane (8).

In one embodiment of the inventive device, as illustrated in FIG. 1, and based upon absorbance type of reagent chemistries, the sensor probe comprises a reaction chamber formed from a semipermeable membrane (8) in tubular form of a small diameter (typically less than 0.5 mm) and sealed at both ends by epoxy or some other means (3). A reagent delivery system causes reagent to flow into the reaction chamber, or lumen of the tubing, via a small diameter capillary made of fused silica or a chemically resistant polymer (6), and drains through a suitable tubing (7) to a waste collection. As reagent flows from the distal to proximal ends of the reaction chamber, analyte can pass through the membrane (8), mix and react with the reagents, forming a colored species that may optically detected.

Figure 2:
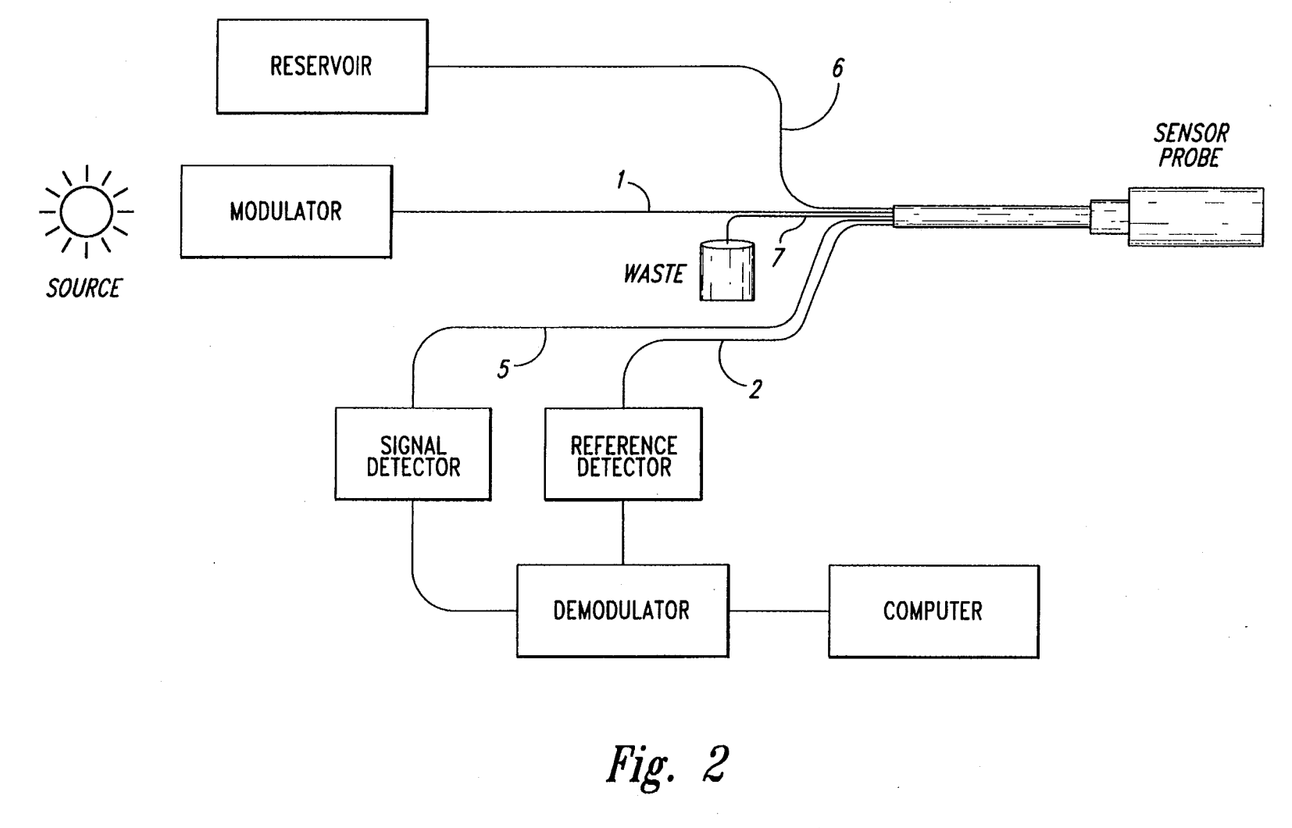

Detection is accomplished via a fiber optic (1) connected to a modulated source as shown in FIG. 2, a source reference fiber (2) and a detection fiber (5) connected to their respective detectors and demodulators in FIG. 2. In the embodiment shown in FIG. 1, fibers 5 and 2 are embedded in a secondary source of electromagnetic radiation which is a transparent epoxy endcap (3). A silver-filled epoxy (or other suitable material) is placed over or mixed in (3) to increase the intensity of back-reflected light and to eliminate effects of external refractive index changes. The epoxy end-cap (3) becomes a secondary source produced by light scattered and back-reflected from the primary electromagnetic radiation source, fiber (1). Fiber 2 is used as a reference for the intensity of the secondary source of electromagnetic radiation at the same modulated signal wavelength. Light or electromagnetic radiation emanating from the end-cap is collected by fiber (5) after traversing the reaction chamber volume and conducts the analyte modulated light signal back to a suitable detector. A computer is used for processing the optical signals as shown in FIG. 2.

An example of how a secondary source of electromagnetic radiation can be created is to embed the distal end of an optical fiber carrying a light from the primary radiation source in translucent epoxy. The epoxy will be illuminated to form the secondary source. Light may then be more effectively directed downward the detection fiber by covering part of the secondary source with a reflective coating, such as a silver-filled epoxy.

When using chemiluminescent reagent chemistries, only the detection fiber for signal collection is needed since no source or reference fiber would be required. The chemiluminescent reaction has the energy needed to cause excitation of a species derived from a chemical reaction. Light is emitted when the excited species decays back to the ground state.

In sensor probe geometries containing two or more fibers, their placement in the sensor probe relative to one another is variable. An example is the detection of a fluorescence modulation in which excitation, emission signal, and reference fibers (a total of three fibers) could all be placed at the same distance from the secondary source within the reaction chamber. The relative positions of reagent delivery capillaries and fibers are also variable and dependent upon reaction conditions, flow rate, and the membrane transport rate of the analyte or analytes.

Figure 3:
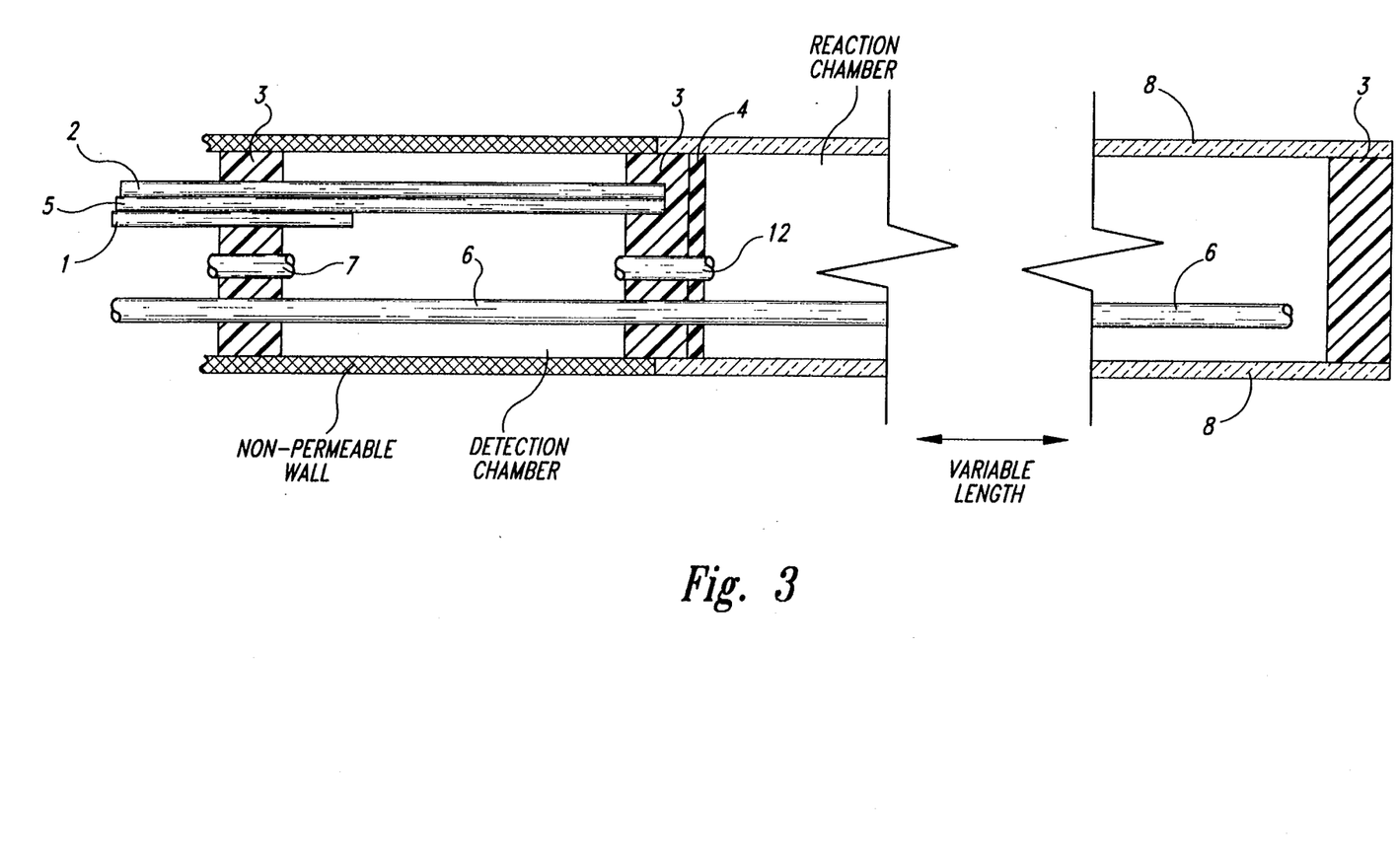
FIG. 3 shows a sensor probe with a variable length to increase the surface area of the permeable membrane (8), increase the volume of the reaction chamber to allow more time for diffusion of the analyte or analytes into the reaction volume and a defined path between the secondary electromagnetic radiation source (3, 4) and the detecting fiber (5). The inflow tube (6) extends through the length of the reaction chamber allowing reagent to flow along the length of the reaction chamber through a tube (12) in the secondary source (3, 4) and into a detection chamber bounded by nonpermeable walls (10) and toward the outflow tube (7). Thus, the sensitivity of this sensor probe is increased due to the increased reaction chamber length and increased surface area of the permeable membrane.
Figure 4:
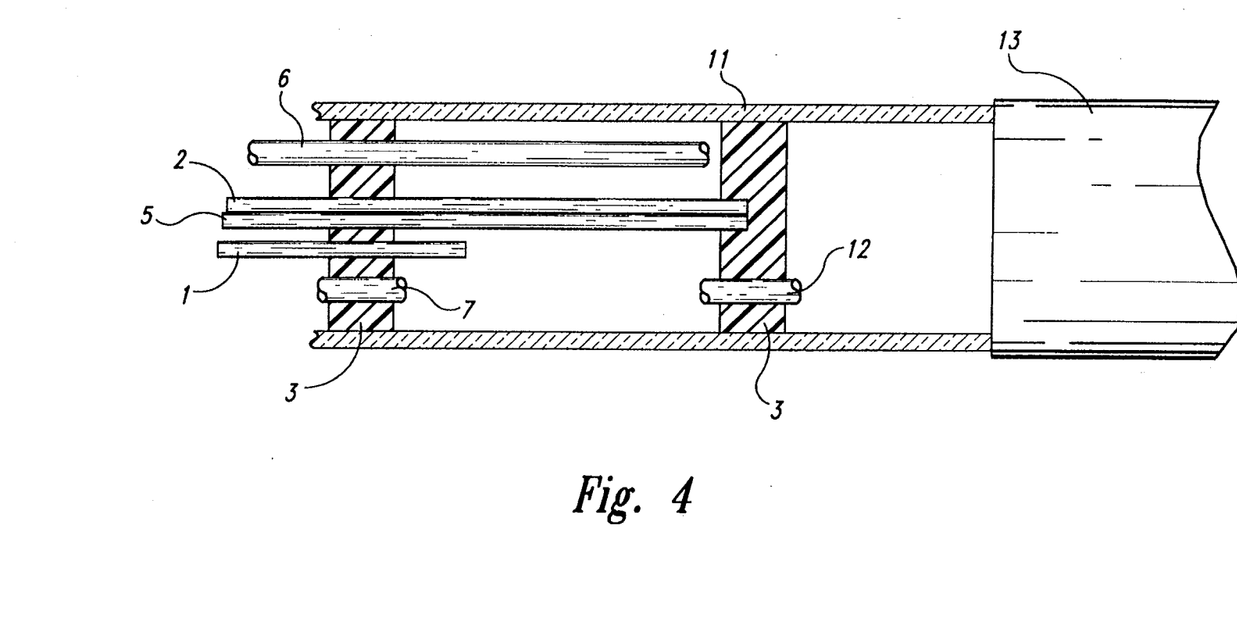
FIG. 4 shows an alternative embodiment of the sensor probe wherein the analyte or analytes enter a reaction chamber via a frit or filtering device (13) and a sampling capillary tube (12). The reaction chamber is defined by nonpermeable barriers (11) and plugs which may be an epoxy filler material, which, at the distal end also acts as the secondary source of electromagnetic radiation (3).

FIG. 3 shows a sensor probe which employs a long length of permeable membrane, which could be coiled into a compact probe to allow for a longer time for signal development before detection. Further, in some process systems, such as those operating above ambient pressure, it is possible to eliminate the permeable membrane from the probe. FIG. 4 illustrates a device in which an open capillary continuously samples the process stream (13). Reagent is added and a signal is developed in the defined path of the optical fibers. A frit may be employed to prevent plugging of the sampling capillary. As in other embodiments of the inventive device, the placement of the optical fibers may be altered, depending upon the spectroscopic technique being employed. When using an embodiment that directly sample analyte from a process stream, the membrane (11) should be impermeable to the diffusion of analyte or analytes.

The following examples are designed to illustrate several aspects of the present invention and are not to be construed to limit the scope of the invention.

EXAMPLE 1

This example illustrates the construction of a device capable of continuously measuring pH in a process stream. The sensor probe was constructed with a visible light source (tungsten filament lamp) as the source of electromagnetic radiation. The light source was modulated at 200 Hz with a mechanical chopper (Stanford Research Systems, Inc., Palo Alto, Calif., Model SR540). The electromagnetic radiation was input into the sensor probe with a source input optical fiber (ensign-Bickford, Avon, Conn., Model HCR-H0110T-14) with a core diameter of 110 μm, a cladding diameter of 125 μm, a buffer diameter of 250 μm and a numerical aperture of 0.48–0.44. The sensor probe was constructed with a detection fiber and a reference fiber from Polymicro Technologies, Phoenix, Ariz., Model FHP 100/110/125 with core diameters of 100 μm, cladding diameters of 110 μm, buffer diameters of 125 μm, and numerical apertures of 0.22. The electromagnetic radiation entering the reference and detection fibers was taken to respective photomultiplier tubes or detection means (Pacific Instruments, Concord, Calif., Model 3150S). Each photomultiplier tube was fitted with 620 nm (maximum absorbance wavelength of the non-protonated form of the reagent, Bromothymol blue) band-pass filters (Microcoatings, Inc., Westford, Mass.). The signals entered respective lock-in amplifiers (Evans Electronics, Berkeley, Calif., Model 4110). All three of the output signals were connected to an AD board of a lock-in amplifier (Stanford Research, Model SR575). This lock-in amplifier was used to acquire, store, and display data on a Leading Edge PC with software written by Stanford Research (SR575 Lock-in Data Acquisition Software).

The bromothymol blue (BTB) reagent was delivered with a high precision microinjection pump (Carnegie-Medicin, Solna, Sweden, Model CMA/100). A 5 mL gas-tight syringe (Hamilton Co., Reno, Nev.) was connected to a 10 cm length of 0.007 inch internal diameter, 0.063 inch outer diameter, Teflon ® (Alltech Associates, Inc., Deerfield, Ill., Flexon HP). The tubing was, in turn, connected to a 1 meter length of 100 μm internal diameter, 165 μm outer diameter fused silica capillary (Polymicro Technologies, Model TSP 100/170) which delivered the reagent to the sensor probe. Microporous hollow fiber membranes were made of polypropylene and had 400 μm internal diameters, 0.03 μm average pore size, 40% porosity and 25 μm wall thickness (Hoechst Celanese, Charlotte, N.C., Model Celgard X-20).

Figure 5:
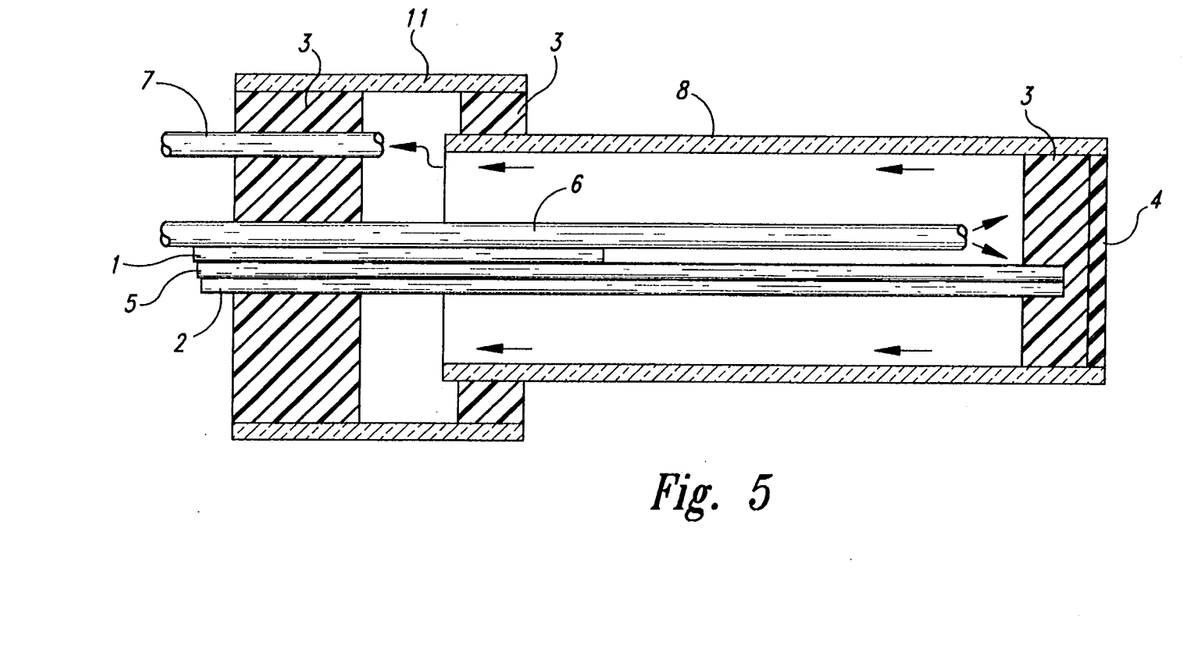
FIG. 5 is a schematic of the sensor probe constructed in Example 1. The arrows show the movement of reagent through the reaction chamber and the movement of analyte across the permeable membrane.

Bromothymol blue (BTB)(Aldrich, Milwaukee, Wis.) was used. All other reagents were analytical grade. A 50 μM BTB solution in the basic form (molar absortivity of 37,000 Lmol$^{-1}$ cm$^{-1}$ at 620 nm) will give an absorbance of 1 unit for a 5 mm defined path length. All solutions were prepared in distilled and deionized water. The sensor probe is shown in a schematic diagram in FIG. 5.

A 12 mm length of polypropylene hollow fiber was placed in a 7 mm length of 1 mm internal diameter glass capillary. The membrane was pushed out of the glass capillary so that 8 mm of the membrane was sticking out. The membrane was then epoxied in this position with a rugged 2-part fluoropolymer epoxy (Master Bond, Hackensack, N.J., Model EP21HTAR). After curing, a bifurcated fiberoptic pair consisting of the electromagnetic source input fiber and the reference fiber (glued together with a Duco Cement-acetone mixture), was pushed through the glass capillary and the hollow fiber membrane until just shy of the end of the membrane. The membrane tip was then filled with fluoropolymer epoxy for a distance of 1 mm. This buries the end faces of the optical fibers, making them impervious to the internal reagent-analyte interaction. After curing, the tip of the membrane was coated with a silver-filled epoxy (Epoxy Technology, Inc., Billerica, Mass., Model EPO-TEK) which serves as a reflective surface of the source electromagnetic radiation. Finally, the membrane tip was dipped in melted black Apeazon wax in order to optically isolate the source and reference fibers from the external environment.

Next, the inflow opening or reagent delivery capillary and the analytical signal fiber were glued together so that the end face of the capillary was 5 mm beyond the end face of the analytical signal fiber. This pair was pushed through the glass capillary and through the open end of the membrane, until the reagent delivery capillary just made contact with the epoxy plug at the tip of the membrane (sensor probe). This step was repeated until the maximum analytical signal level was obtained. The epoxy plug at the tip of the membrane serves as a diffuse secondary source of electromagnetic radiation. Thus, the optical path length or defined path was approximately 5 mm, making the sensing volume of the reaction chamber approximately 400 nL. Finally, a Teflon ® drain tube (0.30 mm internal diameter, 0.76 mm outer diameter, 1 m length) was put into the open end of the glass capillary and that end of the glass capillary was sealed with fluoropolymer epoxy.

This device was capable of continuously measuring the presence and concentration of an analyte, depending upon the reagent used. In the example illustrated herein, the reagent was BTB and the analyte was ammonia.

EXAMPLE 2

This example illustrates the use of the device of Example 1 measuring various ammonia concentrations. Calibration samples were prepared by adding appropriate microliter volumes of ammonium chloride standard to 20 mL aliquots of 0.01M sodium hydroxide. The sensor probe constructed in Example 1 was threaded through a hole in a piece of aluminum stock, which was padded on the bottom. For each sample, before measurement, the vial cap was removed, a stir bar added, and a cap with a hole was put on. The vial was placed in a stir plate which was on a jack. The vial was raised so that the probe passed through the hole in the cap and into the aqueous solution, until the vial cap and padding formed a tight seal. In this way, the integrity of the ammonia concentrations were preserved during measurements. All samples were stirred during measurement. Using the ratio signal output, absorbance values were calculated as log (I/I$_0$) where I and I$_0$ were the sample and incident radiation intensities, respectively. The incident radiation intensity was measured as the signal of a sample solution containing no ammonia.

Since the BTB reagent pumped through the sensor probe is a pH indicator, the response to ammonia becomes a titration curve. The pH transition interval of BTB is between pH 6.0–7.6 for a color change from yellow to blue. In order to obtain maximum sensitivity, it is desirable to have the indicator at an initial pH just below the steepest portion of the titration curve. For a BTB concentration of 50 µM and a continuous flow rate of 5 µL/min, the sensitivity of the probe increased as the pH of the indicator solution increased. However, as the pH increased beyond 5.3, there began to be a decrease in the dynamic range. This is because the probe was operating in the upper portion of the titration curve where the sensitivity to ammonia drops off.

The concentration of the reagent also affected sensitivity. Four concentrations of BTB, each at pH 5.0, were pumped through the sensor probe at a flow rate of 5 µL/min. The results show that sensitivity increased as BTB concentration decreased. The BTB reagent or dye may have been acting as a buffer which is why the sensitivity decreased as the BTB concentration increased. Therefore, as the concentration of the reagent increased, so did the buffer capacity, and as a result, the sensor probe became less sensitive to small changes in ammonia concentration.

Thus, the BTB concentration of 50 µM appeared to be optimal choice. Alternatively, calculation of the optimal BTB concentration which gave absorbances ranging from 0 to 1 absorbance units, based on a 5 mm optical path length and a molar absorptivity at 620 nm of approximately 37,000 $Lmol^{-1} cm^{-1}$, also resulted in a BTB concentration of approximately 50 µM. Based on the results of the reagent pH and concentration studies, the optimal reagent was found to be pH 5.3 and 50 µM BTB.

From the foregoing it will be appreciated that, although specific embodiments of the invention have been described herein for purposes of illustration, various modifications may be made without deviating from the spirit and the scope of the invention.

I claim:

1. A device for continuously measuring an analyte in a liquid or gas sample, comprising:

a sensor probe comprising a first reaction chamber and a second detection chamber downstream from and in fluid communication with the first reaction chamber, wherein the first reaction chamber comprises a permeable membrane separating the reaction chamber from the liquid or gas sample, an inflow opening connecting the reaction chamber to a reagent reservoir, and a reaction chamber outflow opening connecting the first reaction chamber to the second detection chamber, and wherein the second detection chamber is defined by an enclosed space which comprises a primary electromagnetic radiation source fiber, a detection fiber and a detection chamber outflow opening, wherein the primary electromagnetic radiation source fiber is capable of directing electromagnetic radiation across a defined path within the second detection chamber toward the detection fiber, wherein a reagent flows into the first reaction chamber through the inflow opening and contacts the permeable membrane and then flows out of the first reaction chamber and into the second detection chamber by way of the reaction chamber outflow opening where it passes across the defined path within the second detection chamber and flows out the detection chamber outflow opening, wherein the analyte in the liquid or gas sample diffuses across the permeable membrane and into the first reaction chamber, and wherein the first reaction chamber and second detection chamber are both located within the sensor probe;

a reagent reservoir in fluid communication with the inflow opening of the first reaction chamber, wherein the reservoir is capable of containing the reagent, and wherein the reagent chemically reacts with the analyte which diffuses across the permeable membrane to modulate the electromagnetic radiation passing across the defined path differently than reagent alone; and a detection device communicating with the detection fiber of the second detection chamber.

2. The device of claim 1 further comprising a waste reservoir in fluid communication with the detection chamber outflow opening.

3. The device of claim 1 further comprising a secondary source of electromagnetic radiation within the second detection chamber, wherein the secondary source of electromagnetic radiation is a means for scattering or reflecting electromagnetic radiation from the primary electromagnetic radiation source, and wherein the defined path is the distance from the secondary source to the detection fiber.

4. The device of claim 3 wherein the secondary source of electromagnetic radiation is an optically transparent or translucent material that scatters or reflects the electromagnetic radiation.

5. The device of claim 1 wherein the permeable membrane is selected from the group consisting of a semipermeable membrane, an ion exchange membrane and a combination thereof.

6. The device of claim 5 wherein the semi-permeable membrane is made from porous polytetrafluoroethylene, porous polypropylene or silicon rubber.

7. The device of claim 5 wherein the ion exchange membrane is selected from the group consisting of aminated polystyrene, aminated polypropylene, aminated polyethylene, perfluorinated membranes, sulfonated polystyrene polyacrylates and polypropylene, radiation grafted polymers having trimethyl amine, ethyl dimethyl amine and dimethylethanolamine as functional groups, and combinations thereof.

8. The device of claim 1 wherein the electromagnetic radiation is selected from the group consisting of ultraviolet light, visible light, and infrared light.

9. The device of claim 1 wherein the second detection chamber further comprises a source reference detection fiber in communication with the detection device.

10. The device of claim 1 further comprising a means for regulating the rate at which the reagent flows into the first reaction chamber.

11. A method for continuously measuring an analyte in a liquid or gas sample, comprising:

contacting a sensor probe with the liquid or gas sample, wherein the sensor probe comprises a first reaction chamber and a second detection chamber downstream from and in fluid communication with the first reaction chamber, wherein the first reaction chamber comprises a permeable membrane separating the reaction chamber from the liquid or gas sample, an inflow opening connecting the reaction chamber to a reagent reservoir, and a reaction chamber outflow opening connecting the first reaction chamber to the second detection chamber, and wherein the second detection chamber is defined by an enclosed space which comprises a primary electromagnetic radiation source fiber, a detection fiber and a detection chamber outflow opening, wherein the primary electromagnetic radiation source fiber is capable of directing electromagnetic radiation across a defined path within the second detection chamber toward the detection fiber, wherein a reagent flows into the first reaction chamber through the inflow opening and contacts the permeable membrane and then flows out the first reaction chamber and into the second detection chamber by way of the reaction chamber outflow opening where it passes across the defined path within the second detection chamber and flows out the detection chamber outflow opening, wherein the analyte in the liquid or gas sample diffuses across the permeable membrane and into the first reaction chamber, wherein the first reaction chamber and second detection chamber are both located within the sensor probe, and wherein the detection fiber of the second detection chamber is in communication with a detection device;

adjusting the concentration of the reagent and the flow rate at which the reagent flows into the first reaction chamber through the inflow opening; and detecting the analyte in the liquid or gas sample by the analyte diffusing across the permeable membrane and into the first reaction chamber, reacting with the reagent, modulating the electromagnetic radiation directed across the defined path within the second detection chamber, and detecting the modulated signal with the detection device which is in communication with the detection fiber.

12. The method of claim 11 wherein the sensor probe further comprises a waste reservoir in fluid communication with the detection chamber outflow opening.

13. The method of claim 11 wherein the sensor probe further comprises a secondary source of electromagnetic radiation within the second detection chamber, wherein the secondary source of electromagnetic radiation is a means for scattering or reflecting electromagnetic radiation from the primary electromagnetic radiation source, and wherein the defined path is the distance from the secondary source to the detection fiber.

14. The method of claim 13 wherein the secondary source of electromagnetic radiation is an optically transparent or translucent material that scatters or reflects the electromagnetic radiation.

15. The method of claim 11 wherein the second detection chamber further comprises a source reference detection fiber in communication with the detection device.

16. The method of claim 11 wherein the electromagnetic radiation is selected from the group consisting of ultraviolet light, visible light, and infrared light.

17. The method of claim 11 wherein the permeable membrane allows for diffusion of the analyte into the first reaction chamber by passive diffusion through a semipermeable membrane, wherein the composition of the semipermeable membrane is selected from the group consisting of porous polytetrafluoroethylene, porous polypropylene, and silicone rubber.

18. The method of claim 11 wherein the rate at which the reagent flows into the first reaction chamber through the inflow opening is adjusted by a valve communicating with either the inflow opening or the detection chamber outflow opening.

19. The method of claim 11 wherein the detection device measures absorbance, fluorescence or chemiluminescence.

20. A device for continuously measuring an analyte in a liquid or gas sample by chemiluminescence, comprising:

a sensor probe comprising a first reaction chamber and a second detection chamber downstream from and in fluid communication with the first reaction chamber, wherein the first reaction chamber comprises a permeable membrane separating the reaction chamber from the liquid or gas sample, an inflow opening connecting the reaction chamber to a reagent reservoir, and a reaction chamber outflow opening connecting the first reaction chamber to the second detection chamber, and wherein the second detection chamber is defined by an enclosed space which comprises a detection fiber and a detection chamber outflow opening, wherein a reagent flows through the inflow opening and into the first reaction chamber and contacts the permeable membrane and then flows out the first reaction chamber and into the second detection chamber by way of the reaction chamber outflow opening and then flows out the detection chamber outflow opening, wherein the analyte in the liquid or gas sample diffuses across the permeable membrane and into the first reaction chamber where it reacts with the reagent to produce photons by a chemiluminescent reaction, wherein the photons are detected by the detection fiber in the second detection chamber, and wherein the first reaction chamber and the second detection chamber are located within the sensor probe;

a reagent reservoir in fluid communication with the inflow opening of the first reaction chamber wherein the reservoir is capable of containing the reagent; and a detection device in communication with the detection fiber of the second detection chamber and capable of detecting the photons detected by the detection fiber.

21. A method for continuously measuring an analyte in a liquid or gas sample by chemiluminescence, comprising:

contacting a sensor probe with the liquid or gas sample, wherein the sensor probe comprises a first reaction chamber and a second detection chamber downstream from and in fluid communication with the first reaction chamber, wherein the first reaction chamber comprises a permeable membrane separating the reaction chamber from the liquid or gas sample, an inflow opening connecting the reaction chamber to a reagent reservoir, and a reaction chamber outflow opening connecting the first reaction chamber to the second detection chamber, and wherein the second detection chamber is defined by an enclosed space which comprises a detection fiber and a detection chamber outflow opening, wherein a reagent flows through the inflow opening and into the first reaction chamber and contacts the permeable membrane and then flows out the first reaction chamber and into the second detection chamber by way of the reaction chamber outflow opening and flows out the detection chamber outflow opening, wherein the analyte in the liquid or gas sample diffuses across the permeable membrane and into the first reaction chamber where it reacts with the reagent to produce photons by a chemiluminescent reaction, wherein the photons are detected by the detection fiber in the second detection chamber, wherein the first reaction chamber and second detection chamber are located within the sensor probe, and wherein the detection fiber of the second detection chamber is in communication with a detection device;

adjusting the concentration of the reagent and the rate at which the reagent flows into the first reaction chamber through the inflow opening; and detecting the analyte in the liquid or gas sample with the detection device which is in communication with the detection fiber.

22. The method of claim 21 wherein the permeable membrane is a semipermeable membrane which allows for diffusion of the analyte into the first reaction chamber by passive diffusion through the semipermeable membrane, wherein the composition of the semipermeable membrane is selected from the group consisting of porous polytetrafluoroethylene, porous polypropylene, and silicone rubber.

23. The method of claim 21 wherein the detection device is a photomultiplier tube.

* * * * *